(12) United States Patent
Smith (10) Patent No.: US 10,695,075 B2
(45) Date of Patent: Jun. 30, 2020

(54) HANDHELD SURGICAL DEVICE HAVING RETRACTABLE PORTION

(71) Applicant: Michael D. Smith, Tonka Bay, MN (US)

(72) Inventor: Michael D. Smith, Tonka Bay, MN (US)

( * ) Notice: Subject to any disclaimer, the term of this patent is extended or adjusted under 35 U.S.C. 154(b) by 59 days.

(21) Appl. No.: 15/400,476

(22) Filed: Jan. 6, 2017

(65) Prior Publication Data

US 2017/0196573 A1     Jul. 13, 2017

Related U.S. Application Data

(60) Provisional application No. 62/276,007, filed on Jan. 7, 2016.

(51) Int. Cl.
| | |
|---|---|
| *A61B 17/16* | (2006.01) |
| *A61B 17/32* | (2006.01) |
| *A61B 17/3207* | (2006.01) |
| *A61B 90/00* | (2016.01) |
| *A61B 17/00* | (2006.01) |

(52) U.S. Cl.
CPC ...... *A61B 17/1633* (2013.01); *A61B 17/1615* (2013.01); *A61B 17/1622* (2013.01); *A61B 17/32002* (2013.01); *A61B 17/320708* (2013.01); *A61B 2017/00353* (2013.01); *A61B 2017/00367* (2013.01); *A61B 2017/00991* (2013.01); *A61B 2017/320052* (2013.01); *A61B 2090/08021* (2016.02)

(58) Field of Classification Search
CPC ...... A61B 17/320016; A61B 17/32002; A61B 17/1633; A61B 17/1615; A61B 17/1624; A61B 17/32004

USPC .................................. 606/79, 80, 170–171
See application file for complete search history.

(56) References Cited

U.S. PATENT DOCUMENTS

| | | | |
|---|---|---|---|
| 3,937,222 A * | 2/1976 | Banko ................ | A61F 9/00763 606/107 |
| 5,601,583 A | 2/1997 | Donahue et al. | |
| 8,109,956 B2 | 2/2012 | Shadeck | |
| 8,162,966 B2 * | 4/2012 | Connor ............ | A61B 17/32001 606/160 |
| 2003/0055404 A1 * | 3/2003 | Moutafis ............ | A61B 17/1633 604/540 |
| 2004/0191897 A1 | 9/2004 | Muschler | |
| 2005/0054972 A1 * | 3/2005 | Adams ............... | A61B 17/1688 604/22 |

(Continued)

OTHER PUBLICATIONS

International Search Report and Written Opinion, International Patent Application No. PCT/US2017/012529 (15 pages).

*Primary Examiner* — Matthew J Lawson
(74) *Attorney, Agent, or Firm* — Alexander J. Kim; Greenberg Traurig LLP (57) ABSTRACT

A handheld surgical device having a working portion that can be covered or uncovered. The working portion of the handheld surgical device can have an advanced position or a retracted position, which can be controlled by one or more switch(es) at the handle portion of the handheld surgical device. The handheld surgical device can also include a shroud that can cover the working portion having a cutting blade driven by a powered motor. The shroud can also have a cutting edge, which is not driven by the powered motor.

10 Claims, 5 Drawing Sheets

(56) References Cited

U.S. PATENT DOCUMENTS

| | | | |
|---|---|---|---|
| 2005/0197661 A1* | 9/2005 | Carrison | A61B 17/1659 606/79 |
| 2008/0183175 A1* | 7/2008 | Saal | A61B 17/32078 606/84 |
| 2008/0281343 A1 | 11/2008 | Dewey et al. | |
| 2010/0094298 A1* | 4/2010 | Alleyne | A61B 17/025 606/80 |
| 2010/0268236 A1* | 10/2010 | Moutafis | A61B 17/1617 606/84 |
| 2010/0286695 A1* | 11/2010 | Hannani | A61B 17/025 606/80 |
| 2013/0023882 A1* | 1/2013 | Fabro | A61B 17/295 606/80 |
| 2013/0072935 A1* | 3/2013 | Matsuda | A61B 17/32002 606/79 |
| 2014/0031844 A1* | 1/2014 | Kusleika | A61B 17/32075 606/159 |
| 2015/0133984 A1 | 5/2015 | Loreth | |

* cited by examiner

HANDHELD SURGICAL DEVICE HAVING RETRACTABLE PORTION

FIELD

This disclosure relates generally to a handheld surgical device configured for performing one or more surgical procedure(s).

BACKGROUND

Surgical tools are used in the healthcare field to, for example, affect (e.g., cut, remove, cauterize, etc.) an anatomical part during a surgical procedure. Generally, each surgical tool is configured to perform a specific function. Accordingly, it can be necessary for a professional to use multiple surgical tools during a surgical procedure when different functions are needed to complete the surgical procedure.

SUMMARY

The inventor has discovered that when a professional uses multiple surgical tools, manual actions of switching between the two surgical tools can be very time consuming, and can lead to increase in associated costs.

The disclosure herein provides improved handheld surgical devices and methods related to the handheld surgical devices. Some of the embodiments of the handheld surgical devices described herein are configured with a working portion that is covered (e.g., when not being used), and then uncovered (e.g., when it is being used). For example, the working portion can be retracted to be covered when it is not being used, but then the working portion is extended to be uncovered when it is being used. Further, when the working portion is covered, the part that covers the working portion can include another working portion that is configured for performing a different procedure. Thus, some of the embodiments of the handheld surgical devices can be used to perform two or more specific functions. Advantageously, the embodiments of the handheld surgical devices described herein can reduce and/or eliminate the need for switching between surgical devices during performance of a surgical procedure. Thus, there can be savings in time, related costs, or both.

In some embodiments, the handheld surgical device has a distal portion and a proximal portion. The terms "proximal" and "distal" are used herein to indicate portions of the handheld surgical device with respect to an operator's hand. That is, the proximal portion is close to the operator's hand than the distal portion of the handheld surgical device. The proximal portion includes a handle configured for being held by an operator's hand. A switch is disposed at the proximal portion (e.g., handle), and the switch is configured to operate the distal portion so that at least a part of the distal portion covers the working portion. The switch can also be configured operate the distal portion to uncover the working portion.

For example, a single switch can be configured to have two stages, wherein in a first stage, the switch advances the working portion at the distal portion so that the working portion becomes uncovered. The uncovered working portion allows the operator to operate the handheld surgical device to perform a function which the working portion is configured to perform (e.g., drill bone, cut tissue, etc.) In a second stage, the switch retracts the working portion at the distal portion so that the working portion becomes covered. The covered working portion prevents the operator from operating the handheld surgical device to perform the function of the working portion. Thus, when the working portion is covered, the working portion cannot be used by the operator. However, a different portion can be used by the operator to perform a different function. Further, in some embodiment, another portion of the handheld surgical device is configured to protect nearby anatomical part(s) when the uncovered working portion is being used by the operator. In some embodiments, there can be two switches, one switch for uncovering the working portion, and another switch for covering the working portion.

In some embodiments, the working portion includes a cutting blade. The cutting blade can be configured for cutting soft tissue, but not bone.

In some embodiments, the working portion includes a drill. The drill can be configured for cutting bone, drilling into bone, or both.

In some embodiments, the working portion is driven by a motor disposed at the proximal portion connected to a power supply.

In some embodiments, the distal portion of the handheld surgical device which covers the working portion includes a shroud.

In some embodiments, the shroud and/or a part of the distal portion includes a cutting edge, wherein the cutting edge is configured to perform a function that is different from the working portion.

In some embodiments, the cutting edge is configured for cutting soft tissue.

In some embodiments, the working portion is driven by a motor to cut and/or drill bone.

In some embodiments, the cutting edge is operable by manual movement of the operator, and the cutting edge is not driven by a motor.

BRIEF DESCRIPTION OF THE DRAWINGS

References are made to the accompanying drawings that form a part of this disclosure, and which illustrate the embodiments in which the devices and methods described herein can be practiced.

DETAILED DESCRIPTION

Generally, a working portion of a handheld surgical device is configured for performing a specific function during a medical procedure that is performed by a healthcare professional. During the medical procedure, it can be necessary for the healthcare profession to switch between different handheld surgical devices at the same or near an anatomical location, such as a wound. For example, a device for cutting and removing soft tissue may be used, and then, when that device nears a bone, a different device may be needed to cut away the bone. Switching between different handheld surgical devices repeatedly within the wound to complete an operation can increase the operation time and associated costs. Further, switching between different surgical devices may require the healthcare professional to take her eyes off of the anatomical region (e.g., wound) and also may require additional mental concentration in order to acquire the correct tool for the needed function in the anatomical region. Accordingly, alternating between several tools can be tedious and may increase the fatigue of the healthcare professional, risk of contamination, infection, and/or damage to the patient. The contamination, infection, and/or intended damage can cause or exacerbate problems for a patient and a treatment plan. Thus, there is a clear advantage for a handheld surgical device which can reduce and/or eliminate the tedious alternation between different tools.

The handheld surgical devices described herein can provide multiple tools and/or functions in a single device. Thus, the handheld surgical devices described herein can reduce and/or eliminate the tedious alternation between different tools.

An embodiment of a handheld surgical device described herein includes a shroud that extends from a working portion disposed on a distal portion and a cutting blade within a neck portion of the distal portion, from which the cutting blade can be retracted and advanced based on the setting of a switch. The shroud portion of the handheld surgical device can include a cup portion that can function independently of the cutting blade.

Figure 1:
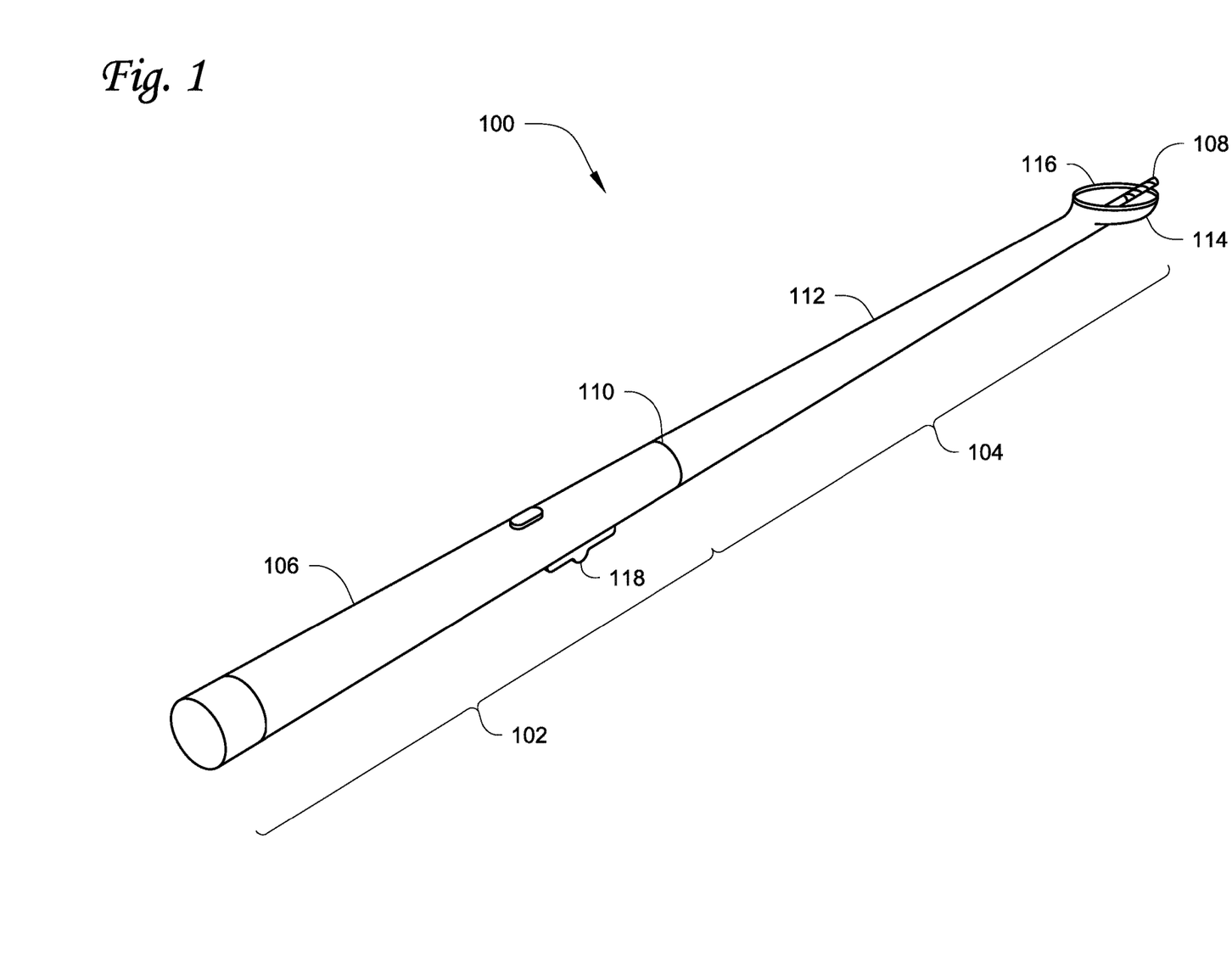
FIG. 1 shows a schematic illustration of an embodiment of the handheld surgical device.

FIG. 1 shows a schematic illustration of a handheld surgical device 100, according to an embodiment. The handheld surgical device 100 includes a proximal portion 102 and a distal portion 104. The proximal portion 102 includes a handle 106 configured for a user's hand to hold, preferably comfortably, while the handheld surgical device 100 is being used. The distal portion 104 includes a working portion 108. At least a part of the working portion 108 is configured for being inserted into a wound or an anatomical area to perform a function (e.g., drill bone, cut tissue, etc.) during a surgical procedure.

In some embodiments, the distal portion 104 can be attached and/or detached from the proximal portion 102 at an attachment region 110. For example, the distal portion 104 can be detached from the proximal portion 102 at the attachment region 110 after use in a surgical procedure, and then a new (i.e., unused) distal portion 104 can be attached to the proximal portion 102 at the attachment region 110 before being used in another surgical procedure. Alternatively, the distal portion 104 can be removed and cleaned/sanitized before being reattached to the proximal portion 102 for future use. That is, the distal portions 104 can be disposed of after use, or be sanitized after use for reuse.

The distal portion 104 includes a neck portion 112, which extends from the attachment region 110 to the working portion 108.

The working portion 108 of the handheld surgical device 100 can be covered by a shroud 114 (or a cover) disposed at or near the end of the distal portion 104. The shroud 114 can be, for example, cup-shaped and have a cutting edge 116. In some embodiments, the shroud 114 can be a concave shaped portion, a hooded cover, or be a partially enclosed scoop. For example, the shroud 114 can be configured for cutting and/or scooping soft tissue, without requiring a powered motor, while the working portion 108 is connected to a motor and a power supply so that the motor drive the working portion 108 so that the working portion 108 can cut or drill into hard tissue and/or bone.

Advantageously, a healthcare professional can use the handheld surgical device 100 for at least two different functions (e.g., for affecting different anatomical regions). Thus, the handheld surgical device 100 can eliminate the need for manually switching between two different surgical tools (e.g., for cutting soft tissue and for cutting bone) during a surgical procedure.

The working portion 108 can be uncovered by the shroud 114 by, for example, being extended outward from the shroud 114. The proximal portion 102 of the handheld surgical device 100 includes a switch 118 disposed at or near the handle 106, wherein the switch 118 can include a first setting for uncovering the working portion 108 and a second setting for covering the working portion 108.

In some embodiments, the length of the working portion 108 is at least 0.5 mm. In some embodiments, the length of the working portion 108 is at least 1.0 mm. In some embodiments, the length of the working portion 108 is at most 10.0 mm. In some embodiments, the length of the working portion 108 can be approximately from 0.5 mm to 10 mm. In some embodiments, the length of the working portion 108 can be approximately from 1 mm to 10 mm.

The handheld surgical device 100 can be of various shapes and sizes.

Figure 2A:
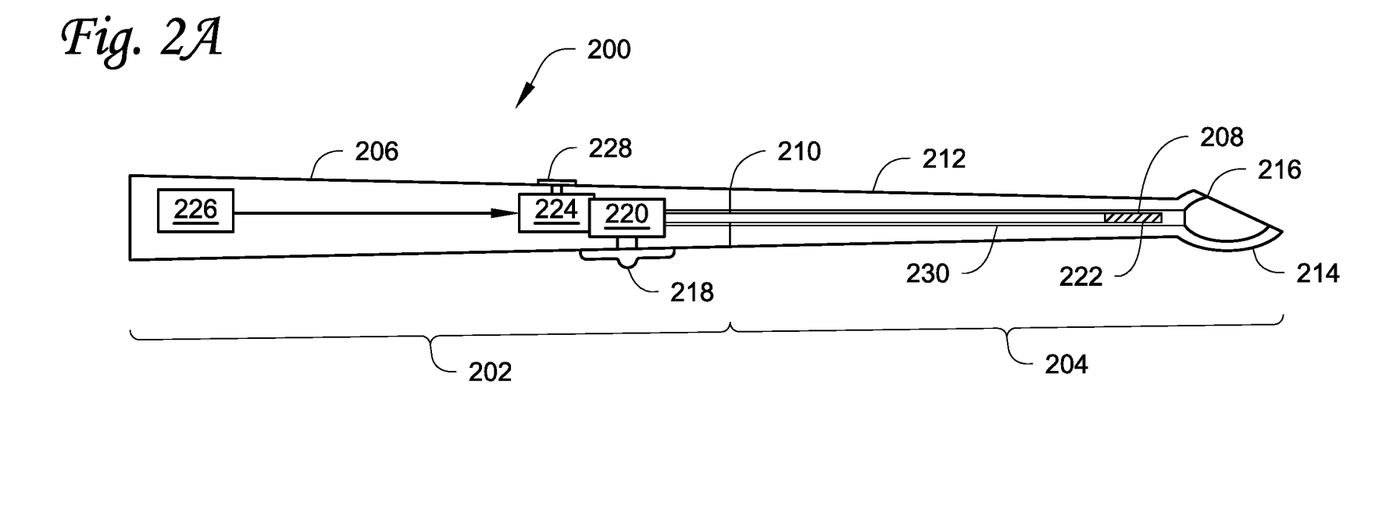
FIGS. 2A and 2B show schematic side views of an embodiment of the handheld surgical device.
Figure 2B:
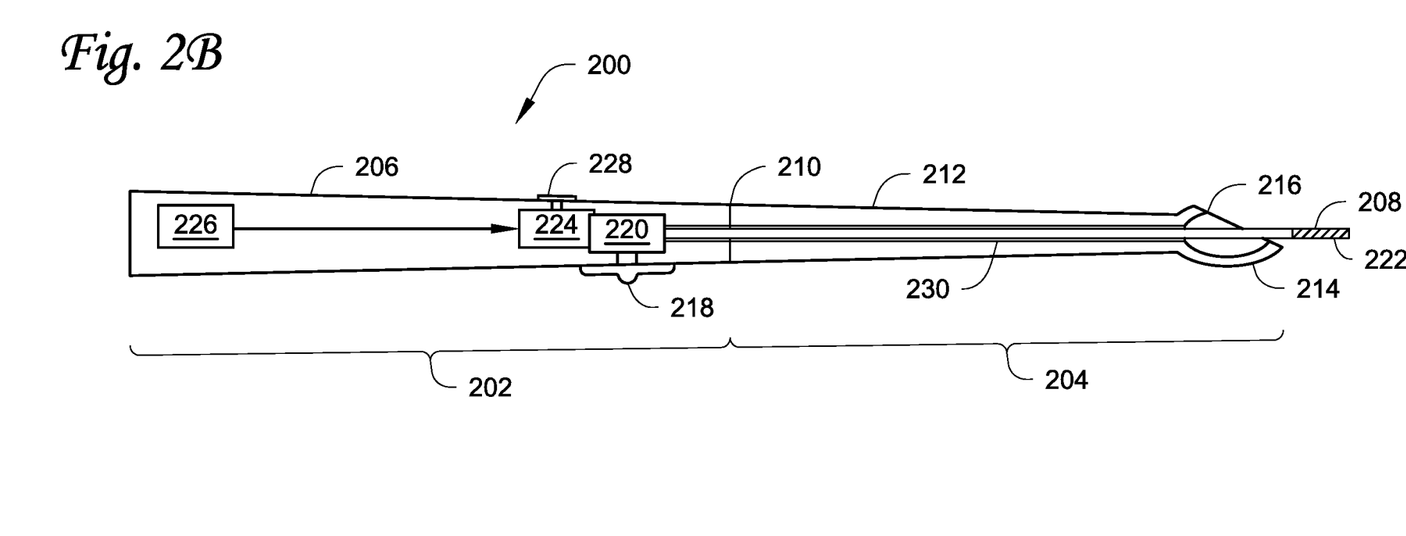

FIGS. 2A and 2B illustrate schematic side views of a handheld surgical device 200, according to an embodiment. The handheld surgical device 200 includes a proximal portion 202, a distal portion 204, a handle 206, a working portion 208, an attachment region 210, a neck portion 212, a shroud 214, a cutting edge 216, and a switch 218, wherein these elements are similar to the like features shown and described with respect to FIG. 1.

The proximal portion 202 includes a mechanism 220 that is connected to the switch 218 and to the working portion 208, wherein the mechanism 220 is configured to change the position of the working portion 208 (e.g., extended position or retracted position) based in a user's input via the switch 218.

The working portion 208 includes a cutting blade 222 driven by a motor 224 that is powered by a power supply 226. The motor 224 and the power supply 226 are disposed in the proximal portion 202. Another switch 228 is configured to activate the motor 224 to drive the cutting blade 222.

FIG. 2A shows the working portion 208 in the retracted position (operable by the switch 218), wherein the working portion 208 is substantially disposed inside a cavity 230 in the neck portion 212. This allows for the cutting edge 216 to be used (e.g., for cutting soft tissue) without being hindered by the working portion 208.

FIG. 2B shows the cutting blade 222 and/or the working portion 208 in the extended position (operable by the switch 218), wherein the cutting blade 222 and/or the working portion 208 is extended out of the cavity 230 and positioned distally away from the cutting edge 216. This allows for the cutting blade 222 and/or the working portion 208 to be used (e.g., for cutting bone) without being hindered by the cutting edge 216. The shroud 214 is disposed at a location away from the cutting blade 222 and/or the working portion 208, so that the shroud 214 can be used to shield and/or protect an anatomical region when the working portion 208 is being used. For example, the position of the shroud 214 with respect to the extended cutting blade 222 and/or extended working portion 208 provides the shroud 214 to be used for pushing away tissue or other anatomical regions that the user does not desire to be affected (e.g., cut, drill, etc.) by the extended cutting blade 222 and/or the extended working portion 208.

In some embodiments, the cutting blade 222 can be a cutting burr made composed of diamond, carbide or like material, and having an oval, matchstick, pear, twist drill, a fluted ball, or the like shape. In some embodiments, the cutting blade 222 can take the shape and/or components of traditional burrs.

When the cutting blade 222 is retracted (e.g., not functioning), the cutting edge 216 of the shroud 214 can function. For example, in an embodiment where the shroud 214 has a cup-like shape (e.g., scoop-shaped), the shroud 214 can be used to scoop and/or gather tissue, bone, blood, and/or the like during the surgical procedure. Further, the cutting edge 216 can function to cut soft tissue, soft bone, and/or a line during the surgical procedure. Because the cutting edge 216 is not powered by a motor, the cutting edge 216 can function to cut soft tissue and/or soft bone. However, the cutting blade 222, which is driven by a motor, can function to cut harder tissue and/or bone.

The power supply 226 can be a battery, a unit for converting AC to DC with a cord for connecting to an AC source, an air pressure unit (i.e., the motor is driven by pressurized air or suction), etc. The power supply 226 can power the motor 224, which can cause the cutting blade 222 to rotate. The cutting blade 222 can rotate at speeds capable of cutting through tissue, bone, or the like during a surgical procedure.

Figure 3:
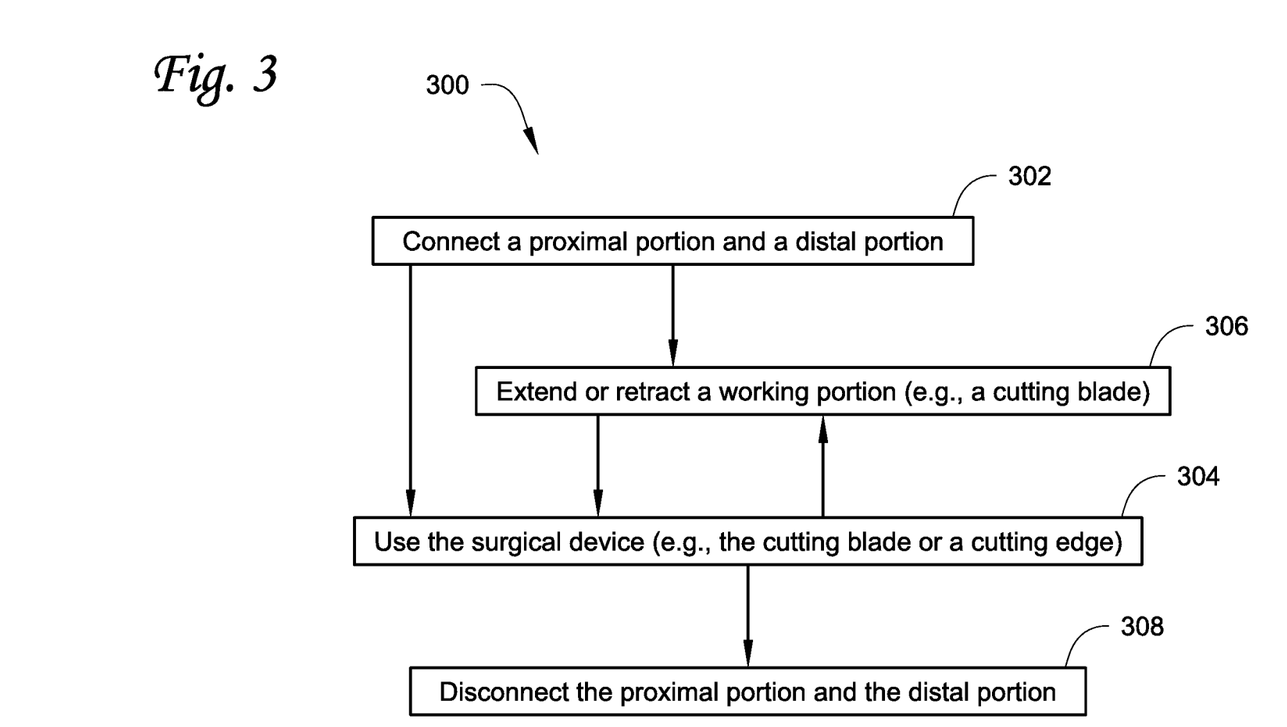
FIG. 3 shows a flowchart of an embodiment of a method of using the handheld surgical device.

FIG. 3 illustrates a method flow diagram 300 for using the handheld surgical device, according to an embodiment. At step 302, a user connects a proximal portion (e.g., 202 shown in FIG. 2A) and a distal portion (e.g., 204 shown in FIG. 2A) of the handheld surgical device (e.g., 200 shown in FIG. 2A). This step 302 can include attaching a different (e.g., new) distal portion to the proximal portion and activating a locking mechanism on the proximal portion to lock the distal portion in place. The different distal portion can be added and/or detached for each new surgical procedure such that the risk of infection and/or contamination is decreased.

At step 304, the user can use the handheld surgical device for cutting tissue, by using a cutting edge or a cutting blade (e.g., the working portion), based on whether the working portion is extended or retracted.

At step 306, the user can extend or retract the working portion, and then at step 304, use the handheld surgical device for cutting tissue or bone, by using the cutting edge or the working portion (e.g., the cutting blade). When the user retracts the working portion so that the working portion is no longer operable, the user can use the handheld surgical device for cutting tissue with the cutting edge. Retracting the cutting blade includes disabling the operation to cut a removal portion with the cutting blade. In some embodiments, retracting the cutting blade completely protects the cutting blade via inside the neck portion of the handheld surgical device. That is, retracting the cutting blade disables the operation to cut a removal portion as it is nestled inside the neck portion of the surgical device and not protected by the shroud, as described herein. In some embodiments, the cutting blade and/or the working portion can be partially protected by a shroud while enabling an operation to cut a removal portion in the anatomy. A removal portion, as used herein, is a portion to be removed and/or cut during a surgical procedure. For example, a removal portion can be an area of bone, tissue, blood, or the like. Additionally, the shroud can partially cover the cutting blade so as to protect areas that are not meant to be cut (e.g., non-removal portions). Step 306 can include powering a motor connected to the cutting blade such that the cutting blade rotates at a speed capable of cutting bone. That is, power can be provided to a motor associated with the cutting blade such that the cutting blade can rotate and cut the removal portion.

At step 308, the user can disconnect the proximal portion and the distal portion. Then the distal portion can be discarded or sanitized for reuse. The distal portion can be removed from the proximal portion at an attachment region, as described herein. Disposing of the distal portion can decrease cross-contamination and/or cross-infection between patients receiving surgical procedures. For instance, using a new distal portion for each patient can significantly reduce contamination and infections risks. In some embodiments, the distal portion can be detached and cleaned before being reattached to the proximal portion. For instance, the distal portion may be detached and cleaned via autoclaving, sanitization procedures, soap, alcohol, and/or the like. The cleaned and/or sanitized distal portion can be reattached to the proximal portion for future use.

The steps shown in FIG. 3 can be performed in various sequences and/or combinations. In particular, the flowchart shown in FIG. 3 provides for performing the steps according to one or more of the exemplary orders and/or sequences listed below (but not necessarily limited only to these orders):

steps 302, 304, and 308;
steps 302, 304, 306, 304, and 308;
steps 302, 306, 304, and 308;
steps 306, and 304;
steps 304, 306, and 304;
steps 304, 306, 304, and 308;
steps 302, 306, and 304;
steps 302, 306, 304, 306, and 304;
steps 302, 304, 306, 304, 306, and 304;
steps 306, 304, and 308;
steps 306, 304, 306, 304, and 308;
steps 304, 306, 304, 306, 304, and 308;
steps 302, 306, 304, and 308;
steps 302, 306, 304, 306, 304, and 308; and
steps 302, 304, 306, 304, 306, 304, and 308.

Figure 4:
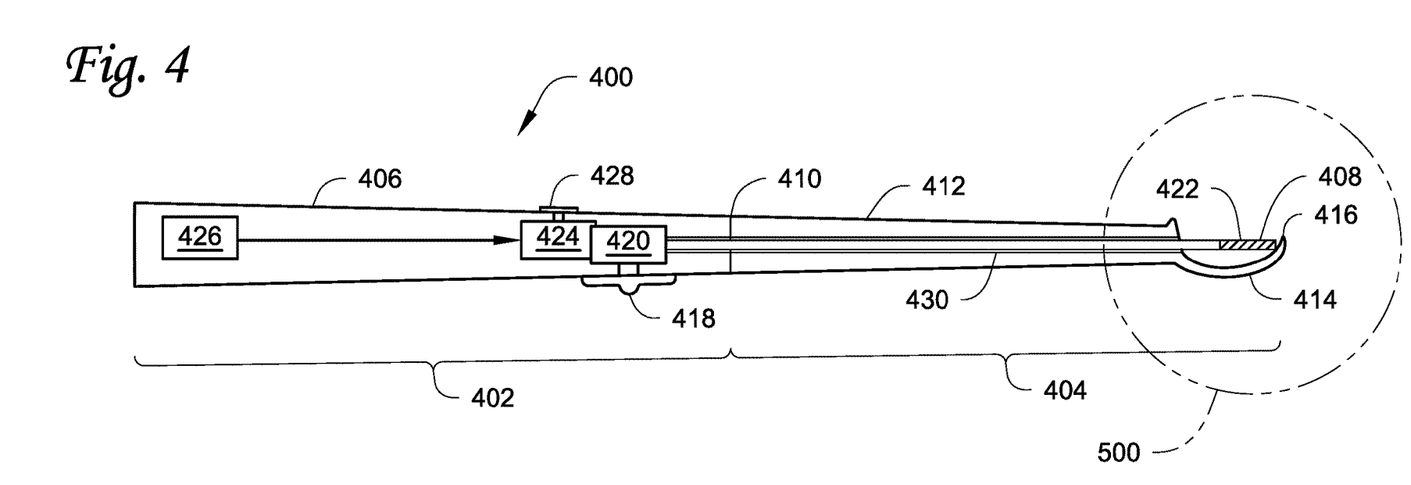
FIG. 4 shows a schematic side view of another embodiment of the handheld surgical device.
Figure 5:
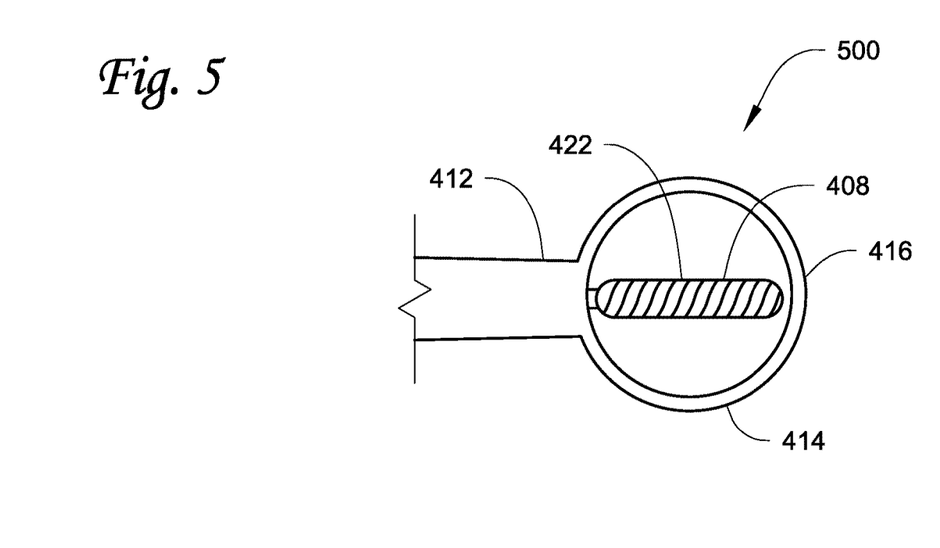
FIG. 5 shows a schematic top view of a portion of the distal portion of the handheld surgical device shown in FIG. 4.

FIG. 4 shows a schematic side view of another embodiment of the handheld surgical device 400. The handheld surgical device 400 includes a proximal portion 402, a distal portion 404, a handle 406, a working portion 408, an attachment region 410, a neck portion 412, a shroud 414, a cutting edge 416, and a switch 418. The proximal portion 402 includes a mechanism 420 that is connected to the switch 418 and to the working portion 408, wherein the mechanism 420 is configured to change the position of the working portion 408 (e.g., extended position or retracted position) based in a user's input via the switch 418. The working portion 408 includes a cutting blade 422 driven by a motor 424 that is powered by a power supply 426. The motor 424 and the power supply 426 are disposed in the proximal portion 402. Another switch 428 is configured to activate the motor 424 to drive the cutting blade 422. The working portion 408 can be placed in the retracted position (operable by the switch 418), wherein the working portion 408 is substantially disposed inside a cavity 430 in the neck portion 412. This allows for the cutting edge 416 to be used (e.g., for cutting soft tissue) without being hindered by the working portion 408. FIG. 4 shows the cutting blade 422 and/or the working portion 408 in the extended position (operable by the switch 418), wherein the cutting blade 422 and/or the working portion 408 is extended out of the cavity 430 and positioned at least partly within a space that is at least partly surrounded by the shroud 414. For example, if the shroud 414 is a concave scoop-like configuration, then at least part of the cutting blade 422 and/or the working portion 408 is contained in the concave scoop-like shape, as shown in FIG. 4. Thus, the shroud 414 can be used to shield and/or protect an anatomical region when the cutting blade 422 and/or the working portion 408 is being used. A top view of a portion 500 of the distal portion 404 is shown in FIG. 5. The portion 500, when viewed from above, shows the cutting blade 422 and/or the working portion 408 contained in the concave scoop-like shape of the shroud 414 when the working portion 408 is in the extended configuration.

Figure 6:
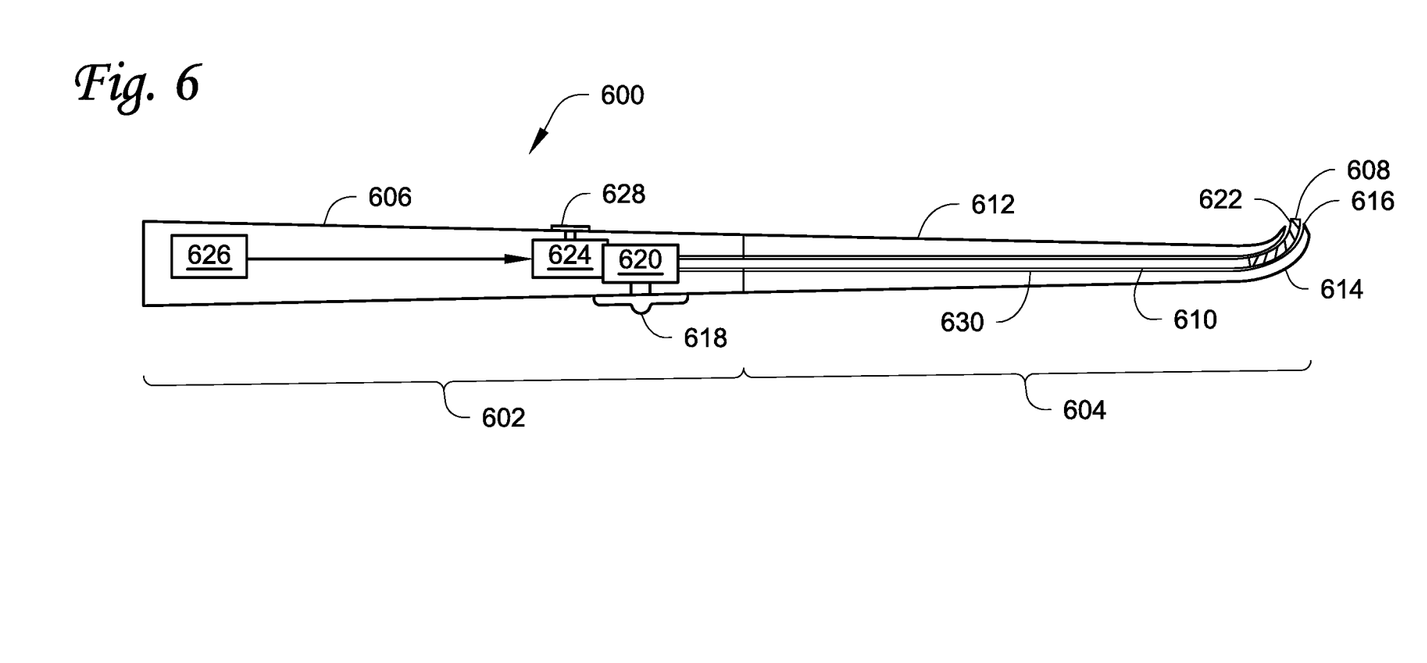
FIG. 6 shows a schematic side view of another embodiment of the handheld surgical device.

FIG. 6 shows a schematic side view of another embodiment of the handheld surgical device. The handheld surgical device 600 includes a proximal portion 602, a distal portion 604, a handle 606, a working portion 608, a shaft 610, a neck portion 612, a shroud 614, a cutting edge 616, and a switch 618. The proximal portion 602 includes a mechanism 620 that is connected to the switch 618 and to the working portion 608, wherein the mechanism 620 is configured to change the position of the working portion 608 (e.g., extended position or retracted position) based in a user's input via the switch 618. The working portion 608 includes a cutting blade 622 driven by a motor 624 that is powered by a power supply 626. The motor 624 and the power supply 626 are disposed in the proximal portion 602. Another switch 628 is configured to activate the motor 624 to drive the cutting blade 622. The working portion 608 can be placed in the retracted position (operable by the switch 618), wherein the working portion 608 is substantially disposed inside a cavity 630 in the neck portion 612. This allows for the cutting edge 616 to be used (e.g., for cutting soft tissue) without being hindered by the working portion 608. FIG. 6 shows the cutting blade 622 and/or the working portion 608 in the extended position (operable by the switch 618), wherein the cutting blade 622 and/or the working portion 608 is extended out of the cavity 630 and positioned at least partly within a space that is at least partly surrounded by the shroud 614. The shroud 614 can be used to shield and/or protect an anatomical region when the cutting blade 622 and/or the working portion 608 is being used. The neck portion 612 is at least partly curved. The shaft 610, which connects to the working portion 608 and the mechanism 620 and/or the motor 626, can be configured to be flexible to follow the curved neck portion 612 within the cavity 630. Alternatively, the shaft 610 is not flexible, but is configured to be guided within the cavity 630 of the curved neck portion 612. In other embodiments, at least a part of the shaft 610 is flexible so that the cutting blade 622 and/or the working portion 608 can be guided to be within the cavity 630 of the curved neck portion 612 when retracted.

The terminology used in this Specification is intended to describe particular embodiments and is not intended to be limiting. The terms "a," "an," and "the" include the plural forms as well, unless clearly indicated otherwise.

With regard to the preceding description, it is to be understood that changes may be made in detail, especially in matters of the construction materials employed and the shape, size, and arrangement of parts without departing from the scope of the present disclosure. The embodiments described are exemplary only. Other and further embodiments may be devised without departing from the basic scope thereof, with the true scope and spirit of the disclosure being indicated by the claims.

What is claimed is:

1. A handheld surgical device, comprising:
   a distal portion including:
   a neck portion including a cavity therein,
   a shroud connected to the neck portion, and
   a working portion configured to cut a bone, drill into the bone, or both cut and drill into the bone, the working portion is configured to move to retract and extend, wherein the working portion is contained in the cavity when retracted, and at least a portion of the working portion is outside of the cavity and disposed beyond the shroud when extended;
   a proximal portion including:
   a handle,
   a motor,
   a power supply to power the motor, and
   a switch being operable to have a cover setting and an uncover setting, wherein in the cover setting, the working portion is retracted and contained in the cavity, and in the uncover setting, the working portion is extended and disposed outside of the cavity,
   wherein the motor is connected to the working portion and drives the working portion,
   the power supply is a battery contained within the proximal portion, the distal portion and the proximal portion are separable, and
   the shroud is cup shaped and includes a cutting edge configured to cut soft tissue.

2. The handheld surgical device according to claim 1, wherein the working portion includes a cutting blade.

3. The handheld surgical device according to claim 2, wherein the cutting blade is a twist drill, oval-shaped, matchstick-shaped, pear-shaped, or fluted ball shaped.

4. The handheld surgical device according to claim 3, wherein the cover setting of the switch prevents the cutting blade from performing a function and enables the shroud to function.

5. The handheld surgical device according to claim 3, wherein the uncover setting provides the cutting blade to perform a cutting function and disables the shroud from the cutting function.

6. The handheld surgical device according to claim 1, wherein the working portion is approximately from 0.5 mm to 10.0 mm.

7. A method of using a handheld surgical device, comprising:
   moving a motor-driven cutting blade to extend out from a cavity in a neck portion of the handheld surgical device by operating a switch disposed at a proximal portion of the handheld surgical device,
   wherein the motor-driven cutting blade is powered by a battery contained within the proximal portion, and at least a portion of the cutting blade becomes exposed beyond a shroud and is operable to cut a removal portion of a bone, to drill into the bone, or both, and
   wherein the shroud is cup-shaped, and the shroud includes a cutting edge configured for cutting soft tissue.

8. The method according to claim 7, further comprising:
   moving the motor-driven cutting blade to retract into the cavity in the neck portion of the handheld surgical device by operating the switch, wherein the cutting blade is protected by the shroud.

9. The method according to claim 7, further comprising powering a motor connected to the cutting blade such that the cutting blade rotates at a speed capable of cutting the bone.

10. A method of assembling a handheld surgical device, comprising:
- providing a proximal portion of the handheld surgical device, wherein the proximal portion includes a motor, and a battery contained within the proximal portion;
- providing a distal portion of the handheld surgical device, the distal portion including:
  - a working portion configured to cut a bone, drill into the bone, or both,
  - the working portion being arranged to be contained in a cavity of the distal portion, and
  - a shroud including a cutting edge configured to cut soft tissue; and
- connecting the proximal portion and the distal portion together so that the working portion and the motor are connected together such that the battery powers the motor to drive the working portion; and
- moving the working portion to extend at least a portion of the working portion out of the cavity and beyond the shroud via operation of a switch disposed in the proximal portion.

\* \* \* \* \*